United States Patent
Konishi et al.

(10) Patent No.: US 8,729,319 B2
(45) Date of Patent: May 20, 2014

(54) METHOD FOR PRODUCING HIGHER ALCOHOL

(75) Inventors: Hiroyuki Konishi, Wakayama (JP);
Takaaki Watanabe, Wakayama (JP);
Keiji Shibata, Wakayama (JP);
Yasuhiro Ishikura, Wakayama (JP);
Takuro Nishimura, Wakayama (JP);
Takanobu Katayama, Iwade (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/879,508

(22) PCT Filed: Dec. 7, 2011

(86) PCT No.: PCT/JP2011/078318
§ 371 (c)(1),
(2), (4) Date: Apr. 15, 2013

(87) PCT Pub. No.: WO2012/077717
PCT Pub. Date: Jun. 14, 2012

(65) Prior Publication Data
US 2013/0217924 A1    Aug. 22, 2013

(30) Foreign Application Priority Data
Dec. 8, 2010 (JP) .................................. 2010-273390

(51) Int. Cl.
*C07C 29/149* (2006.01)
*B01J 21/16* (2006.01)
*C07C 31/125* (2006.01)
*C07C 33/02* (2006.01)
*C07C 33/03* (2006.01)

(52) U.S. Cl.
CPC ............. *C07C 29/149* (2013.01); *C07C 31/125* (2013.01); *C07C 33/02* (2013.01); *C07C 33/03* (2013.01); *B01J 21/16* (2013.01)

USPC .......................................................... 568/885

(58) Field of Classification Search
CPC ...... C07C 29/149; C07C 31/12; C07C 33/02; C07C 33/025; C07C 33/03; B01J 21/165
USPC ......................................................... 568/885
See application file for complete search history.

(56) References Cited

U.S. PATENT DOCUMENTS

| 5,229,346 A | 7/1993 | Mori et al. |
| 6,049,013 A | 4/2000 | Ueoka et al. |

FOREIGN PATENT DOCUMENTS

| JP | 59-118090 A | 7/1984 |
| JP | 5-177140 A | 7/1993 |
| JP | 8-169855 A | 7/1996 |
| JP | 9-52853 A | 2/1997 |
| JP | 10-245351 A | 9/1998 |

OTHER PUBLICATIONS

International search report issued in PCT/JP2011/078318 mailed Mar. 13, 2012.
Yasuda, K. et al., New Edition Yushi Seihin no Chishiki, 1st edition, Feb. 25, 1993, pp. 75-88.
International Preliminary Report on Patentability, issued on Jun. 12, 2013, for International Application No. PCT/JP2011/078318.
Notification of Transmittal of Translation of the International Preliminary Report on Patentability, mailed on Jun. 20, 2013, for International Application No. PCT/JP2011/078318.
Written Opinion of the International Searching Authority, mailed on Mar. 13, 2012, for International Application No. PCT/JP2011/078318.

*Primary Examiner* — Elvis O Price
(74) *Attorney, Agent, or Firm* — Birch, Stewart, Kolasch & Birch, LLP

(57) ABSTRACT

Provided is a method of producing a higher alcohol, comprising a step of hydrogenating a lipid obtained by culturing *Euglena* in the presence of a hydrogenation catalyst.

16 Claims, No Drawings

METHOD FOR PRODUCING HIGHER ALCOHOL

FIELD OF THE INVENTION

The present invention relates to a method of producing a higher alcohol by using *Euglena*.

BACKGROUND OF THE INVENTION

A higher alcohol is used, for example, as a raw material for various kinds of surfactants and in food.

A supply source of the higher alcohol mainly depends on oleaginous plants such as coconut and palm kernels. However, a region in which the oleaginous plant can be grown is limited, and it is concerned that use of arable land for supplying a higher alcohol may compete with use of arable land for supplying food or the like.

It is therefore desired to develop a technology for supplying a higher alcohol without depending on use of the oleaginous plant.

Further, a higher alcohol originating in the oleaginous plant has a widespread distribution in the number of carbon atoms. A surfactant derived from a higher alcohol having 12 to 14 carbon atoms is preferably used as a surfactant, and hence it is necessary to adjust its demand and supply. This is an obstacle to increasing the production amount of a higher alcohol.

Meanwhile, it was found that the protozoan "*Euglena*" produces a lipid with an alkyl group having 14 carbon atoms, and a method of producing a higher alcohol by saponification decomposition of the lipid has been reported (Patent Document 1).

CITATION LIST

Patent Document

[Patent Document 1] JP-A-59-118090
[Patent Document 2] JP-A-5-177140

SUMMARY OF THE INVENTION

The present invention provides a method of producing a higher alcohol, comprising a step of hydrogenating a lipid obtained by culturing *Euglena* in the presence of a hydrogenation catalyst.

EMBODIMENT FOR CARRYING OUT THE INVENTION

*Euglena* is considered to be extremely useful as a raw material for supplying a higher alcohol because of its high proliferative capacity and lipid productivity.

However, a conventional higher alcohol obtained by saponification decomposition has a deep red-brown color and a strong odor peculiar to *Euglena*. When a higher alcohol has a bad color and a nasty odor, the degree of freedom is remarkably limited in incorporating the higher alcohol itself, a surfactant which is a derivative of the higher alcohol, or the like into a detergent composition or the like. Further, the saponification decomposition produces a large amount of fatty-acid soap as a by-product, resulting in a reduction in yield of the higher alcohol, and hence is disadvantageous as an industrial production method for a higher alcohol.

Meanwhile, a hydrogenation method is known as one of the methods of producing a higher alcohol (for example, Patent Document 2). However, the hydrogenation method does not involve the direct hydrogenation of an oil and fat, but generally involves converting an oil or fat to a methyl ester first and purifying the methyl ester, followed by a hydrogenation reaction, and hence it is not always possible to apply the method to a natural lipid containing a large amount of impurities.

Thus, the present invention relates to a provision of a method by which a higher alcohol having a good color and a reduced odor can be efficiently produced from *Euglena*.

The inventors of the present invention made intensive studies in view of achieving the foregoing and found that when a lipid obtained by culturing *Euglena* is subjected to a hydrogenation reaction by using a hydrogenation catalyst, the reaction unexpectedly progresses, yielding a higher alcohol efficiently. Further, the inventors found that not only the reaction progresses but also a higher alcohol having significantly improved color and reduced odor peculiar to *Euglena* is provided.

According to the present invention, it is possible to efficiently provide the higher alcohol having a good color and a reduced odor. The higher alcohol is rich in an alcohol component having 14 carbon atoms, and hence is useful as a raw material for a surfactant. Further, a protozoan which can proliferate easily is used, and hence unlike the case of using an oleaginous plant, a region in which the protozoan is grown is not limited, and the competition with a food application or the like does not occur.

*Euglena* to be used in the present invention is a kind of microalgae belonging to the class Mastigophorea in zoology and to the class Euglenophyceae in botany. Specific examples thereof include *Euglena gracilis*, *Euglena gracilis* var. *bacillaris*, *Euglena viridis*, and *Astasia longa*.

The *Euglena* of the present invention includes variant species and mutant strains of strains having substantially the same mycological properties as the above-mentioned strains.

Of those, *Euglena gracilis*, *Euglena gracilis* var. *bacillaris*, and their variant species and mutant strains are preferable from the viewpoint of easy handling.

The *Euglena* can be cultured by using a conventionally known medium. For example, any of the media described in literatures, such as Cramer-Myers medium, Hutner medium, and Koren-Hutner medium ("*Euglena*, physiology and biochemistry" edited by Shozaburo Kitaoka, Gakkai Shuppan Center Co., Ltd., pages 242 to 243) may be used.

Further, there may be used a solid medium, liquid medium, or the like supplemented with: a carbon source such as glucose, arabinose, xylose, mannose, fructose, galactose, sucrose, maltose, lactose, sorbitol, mannitol, inositol, glycerol, soluble starch, blackstrap molasses, inverted sugar syrup, an assimilable organic acid including acetic acid, or ethanol; and a nitrogen source such as an inorganic or organic ammonium salt including ammonia or an ammonium salt, corn gluten meal, soybean powder, a yeast extract, a meat extract, a fish extract, polypeptone, any of various amino acids, or soybean meal, and as required, further supplemented with: an inorganic salt of phosphoric acid, $Mg^{2+}$, $Ca^{2+}$, $Mn^{2+}$, $Zn^{2+}$, $Fe^{2+}$, $Fe^{3+}$, $Na^+$, $K^+$, or the like; and a vitamin such as vitamin B1 or vitamin B12.

The amount of the *Euglena* inoculated in a medium is not particularly limited, but preferably 1 to 50 mass % (hereinafter, simply referred to as "%"), more preferably 2 to 15% in the medium.

The culture method is not particularly limited and examples thereof include aeration culture, anaerobic culture, agitation culture, shaking culture, and static culture. From the viewpoint of the lipid productivity of the *Euglena*, it is preferable that the *Euglena* be cultured under an aerobic condition and after that cultured under an anaerobic condition.

When the *Euglena* is cultured under an aerobic condition, the culture temperature is preferably 20 to 33° C., more preferably 28 to 30° C. In this case, the initial pH (25° C.) of the medium is preferably 2 to 7, more preferably 3 to 5.

Further, the aeration is preferably 0.01 to 2 L/min, more preferably 0.1 to 0.5 L/min per liter of a culture solution.

The culture period under the aerobic condition is preferably 48 to 720 hours, more preferably 72 to 360 hours.

When the *Euglena* is cultured under an anaerobic condition, the culture temperature is preferably 20 to 33° C., more preferably 28 to 30° C. In this case, the initial pH (25° C.) of the medium is preferably 2 to 11, more preferably 3 to 8.

To prepare an anaerobic condition, one kind of inert gas or a combination of two or more kinds of inert gasses selected from a nitrogen gas, a helium gas, an argon gas, a hydrogen gas, and other inert gasses may be used, and among them, the condition is preferable under a nitrogen gas atmosphere or a carbon dioxide gas atmosphere. The aeration of a nitrogen gas, for example, is preferably 0.01 to 2 L/min per liter of a culture solution.

The culture period under the anaerobic condition is preferably 6 to 360 hours, more preferably 8 to 240 hours.

As a buffering agent for adjusting the pH of a medium, there are given, for example, organic acid salts such as salts of carbonic acid, acetic acid, citric acid, fumaric acid, malic acid, lactic acid, gluconic acid, and tartaric acid, inorganic salts such as salts of phosphoric acid, hydrochloric acid, and sulfuric acid, hydroxides such as sodium hydroxide, ammonia, and ammonia water. Any one of the buffering agents may be used alone or two or more kinds thereof may be used in combination.

The *Euglena* may be cultured in the dark or under light irradiation. The condition of the light irradiation may be a condition which enables photosynthesis, and any of artificial light and solar light may be used. The intensity of the light irradiation is preferably 1,000 to 20,000 Lux, more preferably 2,000 to 8,000 Lux.

Further, the agitation speed and shaking speed may be set in consideration of the damage of cells and are preferably set to 10 to 300 r/min.

After the culture is completed, the alga body is recovered by a usual method such as a centrifugal separation method or filtration, followed by solvent extraction, thereby being able to collect a lipid. In this case, the lipid includes any of a simple lipid, a complex lipid, and a derived lipid.

The simple lipid is an ester produced from a fatty acid and an alcohol, and examples thereof include an ester of a lower alcohol such as methanol or ethanol and a fatty acid, an ester wax of a higher alcohol having 8 to 24 carbon atoms and a fatty acid, and a glyceride, which is an ester of glycerol and a fatty acid.

The complex lipid is a lipid further containing phosphorus, nitrogen, or the like, in addition to a simple lipid and examples thereof include a phospholipid.

The derived lipid is a lipid which is derived from a simple lipid and a complex lipid, and examples thereof include fatty acids, hydrocarbons such as carotenoid and squalene, and derivatives thereof.

The recovered alga body may be used directly or may be subjected to pretreatment prior to the solvent extraction. Examples of the pretreatment applied to the recovered alga body include crushing and disrupting, freezing and thawing, and hydrothermal treatment. As a method for the crushing and disrupting, there are given, for example, ultrasonication, a beads mill (such as Dyno-Mill), French press, and homogenization. As a method for the freezing and thawing, there are given, for example, a method in which an alga body is frozen at −80 to −20° C. and is subsequently thawed at 5 to 80° C. Examples of the hydrothermal treatment include a method in which an alga body is treated at 80 to 350° C. for 0 to 20 minutes.

An organic solvent to be used in the solvent extraction is not particularly limited, and examples thereof include: water; alcohols such as methanol, ethanol, propanol, and butanol; polyhydric alcohols such as ethylene glycol, propylene glycol, and butylene glycol; ketones such as acetone and methyl ethyl ketone; esters such as methyl acetate and ethyl acetate; linear and cyclic ethers such as tetrahydrofuran and diethyl ether; polyethers such as polyethylene glycol; halogenated hydrocarbons such as dichloromethane, chloroform, and carbon tetrachloride; hydrocarbons such as hexane, cyclohexane, and petroleum ether; aromatic hydrocarbons such as benzene and toluene; pyridines; and supercritical carbon dioxide. One of the organic solvents may be used alone or two or more kinds thereof may be used in combination. The solvent extraction may also be repeatedly performed by using different kinds of solvents.

Among them, a mixed solvent of a non-polar solvent and a polar solvent is preferable and a polar solvent containing an alcohol is preferably used, from the viewpoint that the mixed solvent has a high lipid solubility, thus being able to provide a lipid in high yield. A chloroform-methanol mixed solvent is preferable as such mixed solvent.

Further, it is preferable to use a non-polar solvent from the viewpoint of providing a high-purity lipid or improving the reactivity of hydrogenation. Preferred examples of the non-polar solvent include halogenated hydrocarbons, hydrocarbons, and aromatic hydrocarbons, and more preferred examples thereof include hydrocarbons. Preferred examples of the hydrocarbons include hexane.

The lower limit value of the amount of the organic solvent used is, with respect to 1 volume of a recovered alga body, preferably 0.005 volume, more preferably 0.01 volume, even more preferably 0.05 volume, from the viewpoint of extraction efficiency. The upper limit value of the amount of the organic solvent used is, with respect to 1 volume of a recovered alga body, preferably 20 volumes, more preferably 10 volumes, even more preferably 5 volumes, from the viewpoint of the ease of handling.

Any of immersion, decoction, leaching, reflux extraction, supercritical extraction, subcritical extraction, and the like may be used as an extraction method. It is possible to refer to, for example, the methods described in "Biochemical Experimental Method 24, Experimental Method for Plant Lipid Metabolism" (written and edited by Akihiro Yamada, Gakkai Shuppan Center Co., Ltd., pages 3 to 4).

The temperature of the extraction is not particularly limited, but is preferably 10 to 60° C., more preferably 20 to 50° C., from the viewpoint of the lipid solubility.

The lipid obtained by culturing *Euglena* as described above is hydrogenated in the presence of a hydrogenation catalyst, thereby yielding a higher alcohol.

Pretreatment may be applied to the lipid prior to the hydrogenation. Examples of the pretreatment of the lipid include washing treatment with water, washing treatment with such a polar solvent as described above, adsorption treatment with an adsorbent, steaming treatment, and fractionation treatment using column chromatography. Any one of the pretreatments or a combination thereof may be used.

In the washing treatment with water, an acidic aqueous solution or an alkaline aqueous solution may also be used. In order to prepare an acidic aqueous solution or an alkaline aqueous solution, any of the above-mentioned buffering agents for adjusting the pH of a medium may be used. Of those, an acidic aqueous solution is preferably used and an aqueous solution of citric acid is more preferably used, from the viewpoint of improving the color and odor of the higher alcohol.

When an acidic aqueous solution is used as the water, the pH (25° C.) of the acidic aqueous solution is preferably 1 to 6, more preferably 1.5 to 5, even more preferably 2 to 4. The lower limit value of the pH of the acidic aqueous solution is preferably 1, more preferably 1.5, even more preferably 2, from the viewpoint of avoiding the deterioration of the color of the higher alcohol due to the erosion of treatment facilities. The upper limit value of the pH of the acidic aqueous solution is preferably 6, more preferably 5, even more preferably 4, from the viewpoint of improving the color and odor of the higher alcohol.

In the washing treatment of the lipid with water, the amount of the water used is, with respect to the lipid, preferably 0.01 to 50 times by mass, more preferably 0.1 to 30 times by mass, even more preferably 0.5 to 20 times by mass, even more preferably 0.8 to 5 times by mass. The lower limit value of the amount of the water used is, with respect to the lipid, preferably 0.01 times by mass, more preferably 0.1 times by mass, even more preferably 0.5 times by mass, even more preferably 0.8 times by mass, from the viewpoint of removing impurities sufficiently. The upper limit value of the amount of the water used is, with respect to the lipid, preferably 50 times by mass, more preferably 30 times by mass, even more preferably 20 times by mass, even more preferably 5 times by mass, from the viewpoint of preventing the loss of the lipid or the ease of handling.

The temperature of the water is preferably 5 to 100° C., more preferably 20 to 95° C., even more preferably 40 to 90° C. The lower limit value of the temperature of the water is preferably 5° C., more preferably 20° C., even more preferably 40° C., from the viewpoint of removing impurities sufficiently. Further, a condition under which the solidification of an oil or fat does not occur is preferable. The upper limit value of the temperature of the water is preferably 100° C., more preferably 95° C., even more preferably 90° C., from the viewpoint of preventing the loss of the lipid or the ease of handling.

The time of the washing with water is preferably 1 to 120 minutes, more preferably 5 to 60 minutes, even more preferably 10 to 30 minutes.

The lower limit value of the time of the washing with water is preferably 1 minute, more preferably 5 minutes, even more preferably 10 minutes, from the viewpoint of removing impurities sufficiently. The upper limit value of the time of the washing with water is preferably 120 minutes, more preferably 60 minutes, even more preferably 30 minutes, from the viewpoint of the ease of handling.

The washing with water may be performed once or may be repeated a plurality of times (for example, twice or three times). After the washing with water is performed, for example, separation and removal of an aqueous phase by centrifugal separation or the like, distillation of water by performing an operation such as reducing pressure or heating, removal of water by adsorption dehydration or the like may be performed. The content of water remaining in the lipid is, for example, preferably 0.001 to 1%, more preferably 0.001 to 0.1%.

The mechanism of the effect of the washing with water has not been necessarily clarified, but the mechanism probably involves that the washing with water contributes to removing substances responsible for the color and odor of a higher alcohol obtained by hydrogenating the washed lipid and/or precursors of the responsible substances.

Examples of the adsorbent used in the adsorption treatment of the lipid include white clay, activated carbon, diatom earth, and combinations thereof. Of those, white clay, activated carbon, or a combination thereof is preferably used, from the viewpoint of improving the color and odor of the higher alcohol.

The white clay as used herein refers to clay mainly containing montmorillonite. Note that acid clay is usually used frequently in the production process of food though the use of acid clay is not particularly required. Further, some kind of acid clay to which activating treatment has been applied is sometimes called activated clay. The white clay in the present invention includes both acid clay and activated clay. Specific examples thereof include acid clay (GALLEON EARTH series) manufactured by Mizusawa Industrial Chemicals, Ltd.

Activated carbon produced by using any of sawdust, wood chips, wood charcoal, coconut charcoal, coal, peat coal, and the like as a raw material and adopting a known method can be used. Specifically, it is possible to use any of commercially available products such as ZN-50 (manufactured by Hokuetsu Carbon Industry Co., Ltd.), KURARAY COAL GLC, KURARAY COAL PK-D, and KURARAY COAL PW-D (manufactured by Kuraray Chemical Co., Ltd.), Shirasagi AW50, Shirasagi A, Shirasagi M, and Shirasagi C (manufactured by Japan EnviroChemicals, Ltd.).

The temperature of a mixture of the lipid and the adsorbent during the adsorption treatment is preferably 5° C. to 200° C., more preferably 20 to 150° C., even more preferably 40 to 120° C., from the viewpoint of improving the color and odor of the higher alcohol. The lower limit value of the temperature of the mixture is preferably 5° C., more preferably 20° C., even more preferably 40° C., from the viewpoints of removing impurities sufficiently and the ease of handling the mixture. The upper limit value of the temperature of the mixture is preferably 200° C., more preferably 150° C., even more preferably 120° C., from the viewpoints of preventing the loss of the lipid and the ease of handling.

The time of the contact between the lipid and the adsorbent during the adsorption treatment is preferably 1 to 120 minutes, more preferably 5 to 60 minutes, even more preferably 10 to 30 minutes. The lower limit value of the time of the contact is preferably 1 minute, more preferably 5 minutes, even more preferably 10 minutes, from the viewpoint of removing impurities sufficiently. The upper limit value of the time of the contact is preferably 120 minutes, more preferably 60 minutes, even more preferably 30 minutes, from the viewpoint of the ease of handling. The adsorption treatment may be performed under reduced pressure or under normal pressure, but is preferably performed under reduced pressure from the viewpoints of oxidization suppression and decoloration property.

The amount of the adsorbent used during the adsorption treatment is, with respect to 100 parts by mass of the lipid, preferably 0.001 to 10 parts by mass, more preferably 0.01 to 5 parts by mass, even more preferably 0.1 to 3 parts by mass. The lower limit value of the amount of the adsorbent used is, with respect to 100 parts by mass of the lipid, preferably 0.001 part by mass, more preferably 0.01 part by mass, even more preferably 0.1 part by mass, from the viewpoint of improving the color and odor of the higher alcohol. The upper limit value of the amount of the adsorbent used is, with respect to 100 parts by mass of the lipid, preferably 10 parts by mass, more preferably 5 parts by mass, even more preferably 3 parts by mass, from the viewpoint of shortening the time which is necessary for separating the adsorbent.

The adsorption treatment probably involves that substances responsible for the color and odor of a higher alcohol obtained by hydrogenating the treated lipid and/or precursors of the responsible substances are adsorbed by the adsorbents and removed from the lipid, although the substances and precursors are necessarily identified.

Any known hydrogenation catalyst may be used as the hydrogenation catalyst to be used in the present invention. An example thereof is a catalyst containing at least one kind of metal selected from copper, cobalt, chromium, platinum, rhodium, palladium, iridium, and the like. Of those, a copper catalyst is preferable, and there may be suitably used a copper-chromium catalyst, a copper-zinc catalyst, a copper-iron-aluminum catalyst, a copper-silica catalyst, or the like.

The hydrogenation catalyst may be used in the form of a solid catalyst in which a catalytic metal is supported on a support such as carbon (activated carbon), alumina, silica-alumina, silica, barium carbonate, barium sulfate, calcium carbonate, titanium oxide, zirconium oxide, or zeolite.

A commercially available product may be used as the hydrogenation catalyst, or the hydrogenation catalyst may be prepared by a hitherto known method. For example, the supported solid catalyst may be prepared by a precipitation method, an ion-exchange method, an evaporation-to-dryness method, a spray drying method, a kneading method, or the like.

The pressure of hydrogen may be normal pressure, but hydrogenation is preferably performed under increased pressure and is thus performed under a gauge pressure of preferably 0.1 to 35 MPa, more preferably 3 to 30 MPa.

The temperature of the reaction may be suitably selected depending on the activity of the catalyst, and the temperature is preferably 30 to 300° C., more preferably 130 to 270° C., even more preferably 150 to 250° C.

In the present invention, the hydrogenation of the lipid can be performed in the presence of a hydrogenation catalyst according to any of reaction systems such as a batch system, a slurry bed continuous system, and a fixed bed continuous system.

In the case of the batch system, the time of the reaction is preferably 0.5 to 7 hours, more preferably 1 to 6 hours, even more preferably 3 to 5 hours. The amount of the hydrogenation catalyst used can be arbitrarily selected depending on the temperature of the reaction or the pressure of the reaction as long as a practical yield of the reaction results. The amount is, with respect to 100 parts by mass of the lipid, preferably 0.1 to 30 parts by mass, more preferably 0.5 to 20 parts by mass.

In the case of the slurry bed continuous system, the time of the reaction is preferably 0.5 to 7 hours. The time of the reaction refers to the time period for which the lipid is kept at a set temperature of the reaction. The amount of the hydrogenation catalyst used is, with respect to 100 parts by mass of the lipid, preferably 0.1 to 30 parts by mass, more preferably 0.5 to 20 parts by mass.

In the case of the fixed bed continuous system, the liquid hourly space velocity (LHSV) can be arbitrarily determined depending on the condition of the reaction in consideration of productivity and reactivity, and is preferably determined in the range of 0.2 to 5.0 ($Hr^{-1}$).

The hydrogenation reaction may also be performed in the presence of a solvent, but is preferably performed in the absence of a solvent in consideration of productivity. When a solvent is used, it is preferable to use a solvent which does not adversely affect the reaction, such as an alcohol, dioxane, or paraffin.

After the reaction is completed, any of usual separation and purification techniques such as distillation and column separation can be used to isolate and purify an intended higher alcohol. Further, a residue separated from the product after the completion of the reaction can be recovered and used for another hydrogenation reaction as a part of a raw material for the reaction.

In the present invention, the yield of the higher alcohol is preferably 50% or more, more preferably 65% or more, even more preferably 70% or more, from the viewpoint of production efficiency.

The higher alcohol provided by any of the methods of the present invention is a mixture of alcohols with a linear or branched alkyl chain having 12 to 18 carbon atoms. The content of alcohols having 12 to 16 carbon atoms is preferably 90% or more, more preferably 98% or more. Among them, the content of an alcohol having 14 carbon atoms is preferably 40% or more, more preferably 45% or more.

Further, the higher alcohol provided by any of the methods of the present invention has an excellent color. The absorbance thereof measured at a wavelength of 440 nm in a quartz cell having an optical path length of 1 cm is preferably 100 or less, more preferably 50 or less, even more preferably 20 or less, even more preferably 10 or less.

In addition, the higher alcohol provided by any of the methods of the present invention has a reduced odor derived from *Euglena*.

The higher alcohol is useful as a raw material for various surfactants, a softener for synthetic leather, an oil/base for a cosmetic product, a metal rolling oil, and the like.

The present invention further discloses the following production method regarding the above-mentioned embodiment.

<1>

A method of producing a higher alcohol, comprising a step of hydrogenating a lipid obtained by culturing *Euglena* in the presence of a hydrogenation catalyst.

<2>

The method of producing a higher alcohol according to the above-mentioned item <1>, wherein the *Euglena* is *Euglena gracilis, Euglena gracilis* var. *bacillaris*, or a variant species or mutant strain thereof.

<3>

The method of producing a higher alcohol according to the above-mentioned item <1> or <2>, wherein the hydrogenating is performed under normal pressure or under increased pressure, preferably under increased pressure, more preferably under a hydrogen pressure of 0.1 to 35 MPa, even more preferably under a hydrogen pressure of 3 to 30 MPa.

<4>

The method of producing a higher alcohol according to any one of the above-mentioned items <1> to <3>, wherein the hydrogenating is performed at 30 to 300° C., preferably 130 to 270° C., more preferably 150 to 250° C.

<5>

The method of producing a higher alcohol according to any one of the above-mentioned items <1> to <4>, wherein the hydrogenation catalyst is a catalyst comprising at least one kind of metal selected from copper, cobalt, chromium, platinum, rhodium, palladium, and iridium, and is preferably at least one kind of catalyst selected from a copper-chromium catalyst, a copper-zinc catalyst, a copper-iron-aluminum catalyst, and a copper-silic catalyst.

<6>

The method of producing a higher alcohol according to any one of the above-mentioned items <1> to <5>, wherein the hydrogenation catalyst is used in an amount of 0.1 to 30 parts by mass, preferably 0.5 to 20 parts by mass, with respect to 100 parts by mass of the lipid.

<7>

The method of producing a higher alcohol according to any one of the above-mentioned items <1> to <6>, further comprising a step of performing pretreatment of the lipid prior to the hydrogenating.

<8>

The method of producing a higher alcohol according to the above-mentioned item <7>, wherein the pretreatment of the lipid comprises a step of washing the lipid with water.

<9>

The method of producing a higher alcohol according to the above-mentioned item <8>, wherein the lipid is washed with water in an amount of 0.01 times by mass or more, preferably 0.1 times by mass or more, more preferably 0.5 times by mass or more, even more preferably 0.8 times by mass or more, with respect to the lipid.

<10>

The method of producing a higher alcohol according to the above-mentioned item <8> or <9>, wherein the lipid is washed with water in an amount of 50 times by mass or less, preferably 30 times by mass or less, more preferably 20 times by mass or less, even more preferably 5 times by mass or less, with respect to the lipid.

<11>

The method of producing a higher alcohol according to the above-mentioned item <8>, wherein the lipid is washed with water in an amount of 0.01 to 50 times by mass, preferably 0.1 to 30 times by mass, more preferably 0.5 to 20 times by mass, even more preferably 0.8 to 5 times by mass, with respect to the lipid.

<12>

The method of producing a higher alcohol according to any one of the above-mentioned items <8> to <11>, wherein the lipid is washed with water at 5° C. or more, preferably 20° C. or more, more preferably 40° C. or more.

<13>

The method of producing a higher alcohol according to any one of the above-mentioned items <8> to <12>, wherein the lipid is washed with water at 100° C. or less, preferably 95° C. or less, more preferably 90° C. or less.

<14>

The method of producing a higher alcohol according to any one of the above-mentioned items <8> to <11>, wherein the lipid is washed with water at 5 to 100° C., preferably 20 to 95° C., more preferably 40 to 90° C.

<15>

The method of producing a higher alcohol according to any one of the above-mentioned items <8> to <14>, wherein an acidic aqueous solution is used as the water.

<16>

The method of producing a higher alcohol according to the above-mentioned item <15>, wherein the acidic aqueous solution has a pH of 1 or more, preferably 1.5 or more, more preferably 2 or more.

<17>

The method of producing a higher alcohol according to the above-mentioned item <15> or <16>, wherein the acidic aqueous solution has a pH of 6 or less, preferably 5 or less, more preferably 4 or less.

<18>

The method of producing a higher alcohol according to the above-mentioned item <15>, wherein the acidic aqueous solution has a pH of 1 to 6, preferably 1.5 to 5, more preferably 2 to 4.

<19>

The method of producing a higher alcohol according to any one of the above-mentioned items <7> to <18>, wherein the pretreatment of the lipid comprises adsorption treatment with an adsorbent.

<20>

The method of producing a higher alcohol according to the above-mentioned item <19>, wherein the adsorbent used for the adsorption treatment is white clay, activated carbon, diatom earth, or a combination thereof, preferably white clay, activated carbon, or a combination thereof.

<21>

The method of producing a higher alcohol according to the above-mentioned item <19> or <20>, wherein a mixture of the lipid and the adsorbent in the adsorption treatment has a temperature of 5° C. or more, preferably 20° C. or more, more preferably 40° C. or more.

<22>

The method of producing a higher alcohol according to any one of the above-mentioned items <19> to <21>, wherein a mixture of the lipid and the adsorbent in the adsorption treatment has a temperature of 200° C. or less, preferably 150° C. or less, more preferably 120° C. or less.

<23>

The method of producing a higher alcohol according to the above-mentioned item <19> or <20>, wherein a mixture of the lipid and the adsorbent in the adsorption treatment has a temperature of 5° C. to 200° C., preferably 20 to 150° C., more preferably 40 to 120° C.

<24>

The method of producing a higher alcohol according to any one of the above-mentioned items <19> to <23>, wherein the amount of the adsorbent used in the adsorption treatment is 0.001 part by mass or more, preferably 0.01 part by mass or more, more preferably 0.1 part by mass or more, with respect to 100 parts by mass of the lipid.

<25>

The method of producing a higher alcohol according to any one of the above-mentioned items <19> to <24>, wherein the amount of the adsorbent used in the adsorption treatment is 10 parts by mass or less, preferably 5 parts by mass or less, more preferably 3 parts by mass or less, with respect to 100 parts by mass of the lipid.

<26>

The method of producing a higher alcohol according to any one of the above-mentioned items <19> to <23>, wherein the amount of the adsorbent used in the adsorption treatment is 0.001 to 10 parts by mass, preferably 0.01 to 5 parts by mass, more preferably 0.1 to 3 parts by mass, with respect to 100 parts by mass of the lipid.

EXAMPLES

Analysis Method

A sample was appropriately diluted and extracted with chloroform, followed by analysis by gas chromatography (GC).

Conditions for the GC analysis are as follows.

Column: Ultra ALLOY-1 (MS/HT) manufactured by Frontier Laboratories Ltd.

Oven temperature: 60° C. (2 min hold)-[10° C./min.]-350° C. (15 min hold)

Carrier gas: He, 5.8 mL/min

Injector: split ratio 14:1, inlet temperature 300° C.

Measurement of pH of 50% Aqueous Solution of Citric Acid

A 50% aqueous solution of citric acid as it is was subjected to measurement for its pH at 25° C. by using a pH meter (D-51S manufactured by HORIBA, Ltd.).

Calculation Method for Yield

The yield of a higher alcohol was calculated on the basis of the following equation.

Yield of higher alcohol(%)=mass of higher alcohol/mass of pretreated *Euglena* lipid×100

Evaluation of Color

A sample was diluted with hexane and the absorbance of the diluted sample at a wavelength of 440 nm was measured by using a quartz cell having an optical path length of 1 cm (ultraviolet-visible spectrophotometer, Hitachi, Ltd., U-2000). The measured value was multiplied by the dilution factor to calculate the absorbance of the undiluted solution, and as the calculated value was smaller, the sample was determined to have a better color.

Evaluation of Odor

Evaluation was performed by a panel of eight members in accordance with the following criteria in which the score 5 represented the evaluation of the odor of a raw material (water-washed *Euglena* lipid). The average value of the scores of the members was defined as an evaluation value.
6: Having a very strong odor
5: Having a strong odor
4: Having a slightly strong odor
3: Having a slight odor
2: Having almost no odor
1: Having no odor

Production Example 1

Production of Lipid

20 L of a medium containing 400 g of glucose, 100 g of polypeptone, 5 g of ammonium sulfate, 5 g of monopotassium phosphate, 10 g of magnesium sulfate heptahydrate, 2.4 g of calcium carbonate, 1 g of Na2EDTA, 1 g of ammonium iron(II) sulfate hexahydrate, 0.5 g of zinc sulfate, 0.4 g of manganese sulfate pentahydrate, 0.05 g of thiamine hydrochloride, and 0.00002 g of cyanocobalamin was loaded into a jar fermenter having a volume of 30 L, and the pH of the medium was adjusted to 4 with 1N hydrochloric acid, followed by sterilization (at 121° C. for 30 minutes).

To the resultant mixture, a culture solution of *Euglena gracilis* which had been pre-cultured in another medium having the same composition as the medium was inoculated at 4%, and *Euglena gracilis* was subjected to aeration-agitation culture at 28° C. in the dark for 4 days. In this case, the culture was performed at an aeration flow rate of 6.6 L-air/min and an agitation rotation speed of 153 r/min.

After that, the culture was further continued for 8 days under the same conditions as described above, except that the aeration was performed with nitrogen instead of air at 1 L-$N_2$/min. The initial pH was 3.

Note that the *Euglena* used is *Euglena gracilis* NIES-48 supplied from the Microbial Culture Collection at the National Institute for Environmental Studies, and the same strain is available upon request.

12 days after the start of the culture, *Euglena* cells were recovered by centrifugal separation. Next, 3.75 volumes of a 20° C. chloroform-methanol mixed liquid (chloroform:methanol=(volume ratio) 1:2) were added to 1 volume of the resultant recovered cake, and the mixture was left to stand still for 30 minutes. After that, 1.25 volumes of chloroform and 1% KCl were added respectively, followed by mixing of the whole. After the mixture was left to stand still, the chloroform layer was recovered, followed by evaporation of the chloroform, yielding *Euglena* lipid.

Production Example 2

Production of Lipid

A medium having the same composition as that in Production Example 1 was used. To 1,200 L of the medium, a culture solution of *Euglena gracilis* which had been pre-cultured in another medium having the same composition as the medium was inoculated at 5%, and *Euglena gracilis* was subjected to aeration-agitation culture at 28° C. in the dark for 4 days.

After that, the culture was further continued for 8 days under the same conditions as those of Production Example 1, except that the aeration was performed with nitrogen instead of air.

12 days after the start of the culture, *Euglena* cells were recovered by centrifugal separation. Next, 9 volumes of 20° C. hexane were added to 1 volume of the resultant recovered cake, and the mixture was agitated for two hours and subsequently left to stand still for 24 hours. After that, the hexane layer was recovered, followed by evaporation of the hexane from the hexane layer, yielding *Euglena* lipid.

Example 1

(1) 1 time by mass of 60° C. heated water was added to the *Euglena* lipid produced in Production Example 1, the mixture was heated to 70° C. in a hot bath, and washing was performed for 20 minutes while the mixture was agitated.

After that, the whole was transferred into a centrifuge tube and was subjected to centrifugal separation at 7,000 r/min for 20 minutes.

The oil phase was taken out from the centrifuge tube and was subjected to dehydration treatment while being agitated under the conditions of 105° C. and 8 kPa. This lipid was referred to as "water-washed *Euglena* lipid." The yield ratio of the water-washed *Euglena* lipid was 87% with respect to the *Euglena* lipid.

The water content of the resultant water-washed *Euglena* lipid was 0.1%.

(2) In accordance with the method described in Example 5 of Patent Document 2 (JP-A-5-177140), there was obtained catalyst precursor powder in which CuO, ZnO, and BaO were supported on $TiO_2$. The resultant precursor powder was subjected to tablet compression into a cylindrical shape. After that, the resultant was fired at 400° C. for two hours, providing a formed catalyst precursor with a diameter of 3 mm and a height of 3 mm having the following composition.

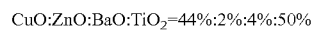

$CuO:ZnO:BaO:TiO_2=44\%:2\%:4\%:50\%$ 30 g (weight in terms of oxides) of the resultant formed catalyst precursor was subjected to activation treatment under a hydrogen atmosphere and was loaded into a 500-mL autoclave together with 180 g of the water-washed *Euglena* lipid described above. After that, hydrogen was passed through the autoclave at 5 NL/min, and a reaction was performed for five hours under the conditions of 250° C. and 22.5 MPa (gauge pressure) while the mixture was agitated at 800 r/min, yielding a higher alcohol.

The results of the GC analysis of the oil after the completion of the reaction showed that the amount of the higher alcohol yielded was 121 g. The yield of the higher alcohol was 67% on the basis of the water-washed *Euglena* lipid.

Table 1 shows the analysis values of the composition of the higher alcohol, and Table 2 shows the results of the color and odor evaluations.

Example 2

(1) 0.9 g of a 50% aqueous solution of citric acid (having a pH of 2.4) was added to 230 g of the *Euglena* lipid produced in Production Example 2, and the mixture was agitated at 90° C. for 20 minutes. After that, 5.5 g of water was added and the whole was further agitated at 90° C. for five minutes. After that, the whole was transferred into a centrifuge tube and was subjected to centrifugal separation at 3,000 rpm/min for 10 minutes.

The upper layer was taken out from the centrifuge tube, yielding 222 g of *Euglena* lipid. This lipid was referred to as "water-washed *Euglena* lipid."

(2) A hydrogenation reaction was performed in the same manner as that in Example 1 (2), except that the water-washed *Euglena* lipid produced in the above-mentioned item (1) was used, yielding a higher alcohol.

The results of the GC analysis of the oil after the completion of the reaction showed that the amount of the higher alcohol yielded was 146 g. The yield of the higher alcohol was 81% on the basis of the water-washed *Euglena* lipid.

Table 2 shows the results of the color and odor evaluations.

Example 3

(1) 4.6 g of activated clay (manufactured by Mizusawa Industrial Chemicals, Ltd.) was added to 230 g of the *Euglena* lipid produced in Production Example 2, and the mixture was agitated at 120° C. and 8 kPa for 20 minutes. After that, the whole was subjected to filtration to remove the activated clay, yielding 218 g of *Euglena* lipid. This lipid was referred to as "white clay-treated *Euglena* lipid."

(2) A hydrogenation reaction was performed in the same manner as that in Example 1 (2), except that the white clay-treated *Euglena* lipid was used in place of the water-washed *Euglena* lipid, yielding a higher alcohol.

The results of the GC analysis of the oil after the completion of the reaction showed that the amount of the higher alcohol yielded was 147 g. The yield of the higher alcohol was 81% on the basis of the white clay-treated *Euglena* lipid.

Table 2 shows the results of the color and odor evaluations.

Example 4

(1) 4.6 g of activated carbon (manufactured by Sigma-Aldrich Co. LLC) was added to 230 g of the *Euglena* lipid produced in Production Example 2, and the mixture was agitated at 60° C. for 1 hour. After that, the whole was subjected to filtration to remove the activated carbon, yielding 224 g of *Euglena* lipid. This lipid was referred to as "activated carbon-treated *Euglena* lipid."

(2) A hydrogenation reaction was performed in the same manner as that in Example 1 (2), except that the activated carbon-treated *Euglena* lipid was used in place of the water-washed *Euglena* lipid, yielding a higher alcohol.

The results of the GC analysis of the oil after the completion of the reaction showed that the amount of the higher alcohol yielded was 146 g. The yield of the higher alcohol was 81% on the basis of the activated carbon-treated *Euglena* lipid.

Table 2 shows the results of the color and odor evaluations.

Comparative Example 1

Saponification of Lipid 10 g of water-washed *Euglena* lipid produced in the same manner as that in Example 1 was added to 250 mL of an aqueous solution of 1N potassium hydroxide and 95% ethanol, and the whole was left to stand at 85° C. for 3 hours to carry out a saponification reaction.

250 mL of water was added to the reaction solution, and the whole was cooled to room temperature and was subjected to extraction twice by using 250 mL of hexane. 500 mL of the extraction liquid was concentrated and dried, yielding an oil after the completion of the reaction containing 3.9 g of a higher alcohol. The yield of the higher alcohol was 39% on the basis of the water-washed *Euglena* lipid. Table 2 shows the results of the color and odor evaluations.

Comparative Example 2

(1) 1 time by mass of 60° C. heated water was added to the oil after the completion of the reaction, containing the higher alcohol produced in Comparative Example 1, the mixture was heated to 70° C. in a hot bath, and washing was performed for 20 minutes while the mixture was agitated. After that, the whole was transferred into a centrifuge tube and was subjected to centrifugal separation at 7,000 r/min for 20 minutes.

The oil phase was taken out from the centrifuge tube and was subjected to dehydration treatment while being agitated under the conditions of 60° C. and 25 torr. Table 2 shows the results of the color and odor evaluations.

TABLE 1

| Alkyl composition (%) | | | | |
| --- | --- | --- | --- | --- |
| C12:0 | C13:0 | C14:0 | C15:0 | C16:0 |
| 1 or less | 13 | 53 | 11 | 15 |

TABLE 2

| | | Example 1 | Example 2 | Example 3 | Example 4 | Comparative Example 1 | Comparative Example 2 |
| --- | --- | --- | --- | --- | --- | --- | --- |
| Evaluation | Color | 2.3 | 0.2 | 0.2 | 0.3 | 178.0 | 114.0 |
| | Odor | 2.1 | 1.6 | 1.7 | 2.4 | 4.0 | 4.0 |

As described above, each higher alcohol produced according to the method of the present invention was found to be a high-quality higher alcohol having a good color and having a reduced odor peculiar to *Euglena*. Further, the yield (yield ratio) of the higher alcohol produced according to the method of the present invention was high, and hence the method was found to be sufficiently efficient as a production method.

On the other hand, each higher alcohol which resulted from saponification had a red-brown color, had a strong odor, and showed low yield. Further, even though the higher alcohol was further washed with water after the saponification, the higher alcohol still had a strong color and a strong odor.

The invention claimed is:

1. A method for producing a higher alcohol, comprising a step of performing pretreatment of a lipid obtained by culturing *Euglena* and a step of hydrogenating the pretreated lipid in the presence of a hydrogenation catalyst.

2. The method for producing a higher alcohol according to claim 1, wherein the pretreatment of the lipid comprises a step of washing the lipid with water.

3. The method for producing a higher alcohol according to claim 2, wherein the lipid is washed with water in an amount of 0.01 to 50 times by mass with respect to the lipid.

4. The method for producing a higher alcohol according to claim 2, wherein the lipid is washed with water at 5 to 100° C.

5. The method for producing a higher alcohol according to claim 2, wherein an acidic aqueous solution is used as the water.

6. The method for producing a higher alcohol according to claim 5, wherein the acidic aqueous solution has a pH of 1 to 6.

7. The method for producing a higher alcohol according to claim 5, wherein the acidic aqueous solution is an aqueous solution of citric acid.

8. The method for producing a higher alcohol according to claim 1, wherein the pretreatment of the lipid comprises adsorption treatment with an adsorbent.

9. The method for producing a higher alcohol according to claim 8, wherein a mixture of the lipid and the adsorbent in the adsorption treatment has a temperature of 5° C. to 200° C.

10. The method for producing a higher alcohol according to claim 8, wherein the adsorbent is white clay.

11. The method for producing a higher alcohol according to claim 8, wherein the adsorbent is activated carbon.

12. The method for producing a higher alcohol according to claim 8, wherein the adsorbent is a combination of white clay and activated carbon.

13. The method for producing a higher alcohol according to claim 1, wherein the hydrogenating is performed under a hydrogen pressure of 0.1 to 35 MPa.

14. The method for producing a higher alcohol according to claim 1, wherein the hydrogenating is performed at 30 to 300° C.

15. The method for producing a higher alcohol according to claim 1, wherein the hydrogenation catalyst is a catalyst comprising at least one kind of metal selected from the group consisting of copper, cobalt, chromium, platinum, rhodium, palladium and iridium.

16. The method for producing a higher alcohol according to claim 1, wherein the hydrogenation catalyst is used in an amount of 0.1 to 30 parts by mass with respect to 100 parts by mass of the lipid.

* * * * *